United States Patent
Gutsmann et al.

(10) Patent No.: US 9,451,764 B2
(45) Date of Patent: Sep. 27, 2016

(54) COMPOSITION COMPRISING INSECTICIDE-WAX PARTICLES

(75) Inventors: Volker Gutsmann, Langenfeld (DE); Thomas Bocker, Leichlingen (DE); Guenther Nentwig, Leverkusen (DE); Rainer Sonneck, Leverkusen (DE); Beate Hack, Cologne (DE); Daniel Gordon Duff, Leverkusen (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 765 days.

(21) Appl. No.: 13/330,376

(22) Filed: Dec. 19, 2011

(65) Prior Publication Data

US 2012/0156273 A1 Jun. 21, 2012

Related U.S. Application Data

(60) Provisional application No. 61/442,445, filed on Feb. 14, 2011.

(30) Foreign Application Priority Data

| Dec. 17, 2010 | (EP) | .................................. 10195657 |
| Apr. 14, 2011 | (EP) | .................................. 11162403 |

(51) Int. Cl.

| *A01N 25/26* | (2006.01) |
| *A01N 43/30* | (2006.01) |
| *A01N 53/00* | (2006.01) |
| *A01P 7/04* | (2006.01) |
| *A01N 25/04* | (2006.01) |
| *A01N 25/28* | (2006.01) |

(52) U.S. Cl.
CPC ............... *A01N 25/04* (2013.01); *A01N 25/26* (2013.01); *A01N 25/28* (2013.01)

(58) Field of Classification Search
CPC ....... A01N 25/26; A01N 25/28; A01N 25/04
See application file for complete search history.

(56) References Cited

U.S. PATENT DOCUMENTS

| 2,564,606 | A | * | 8/1951 | Percy et al. .................. 514/750 |
| 4,882,167 | A | | 11/1989 | Jang |
| 6,001,346 | A | | 12/1999 | Delwiche et al. |
| 2008/0003197 | A1 | | 1/2008 | Bette |

FOREIGN PATENT DOCUMENTS

| CA | 2359491 | * | 2/2000 | ............ A01N 57/00 |
| DE | 1207144 | | 12/1965 | |
| EP | 0021477 | | 1/1981 | |
| EP | 0721734 | * | 7/1996 | ............ A01N 25/12 |
| JP | 5305226 | | 11/1993 | |
| JP | 7242502 | | 9/1995 | |
| JP | 2000351705 | | 12/2000 | |
| WO | WO 95/09532 | | 4/1995 | |
| WO | WO 95/28835 | | 11/1995 | |
| WO | WO 95/34200 | | 12/1995 | |
| WO | WO 97/35476 | | 10/1997 | |
| WO | WO 00/49107 | | 8/2000 | |
| WO | WO 03/045877 | | 6/2003 | |
| WO | WO 2006/117158 | | 11/2006 | |
| WO | WO 2010/031508 | | 3/2010 | |

OTHER PUBLICATIONS

"395" Flumethrin In: McBean C: "The e-Pesticide Manual (15 edition) v. 5.0.1", May 1, 2010, British Crop Protection Council (BCPC), XP002629121.
"586" Flumethrin In: McBean C: "The e-Pesticide Manual (15 edition) v. 5.0.1", May 1, 2010, British Crop Protection Council (BCPC), XP002629122.
International Search Report of PCT/EP2011/072484, mailed Mar. 2, 2012.
Extended European Search Report of European Application No. 10195657.1 mailed Apr. 27, 2011.

* cited by examiner

*Primary Examiner* — Mina Haghighatian
*Assistant Examiner* — Helen Chui
(74) *Attorney, Agent, or Firm* — Arent Fox LLP

(57) ABSTRACT

The present invention relates to compositions for pest control, more particularly insecticides, to a process for preparing them, and to the use of such formulations for sustained control of animal pests (arthropods) on various surfaces. The present invention further relates to active ingredient-wax particles in which at least one active insecticidal ingredient is dispersed in wax.

8 Claims, 1 Drawing Sheet

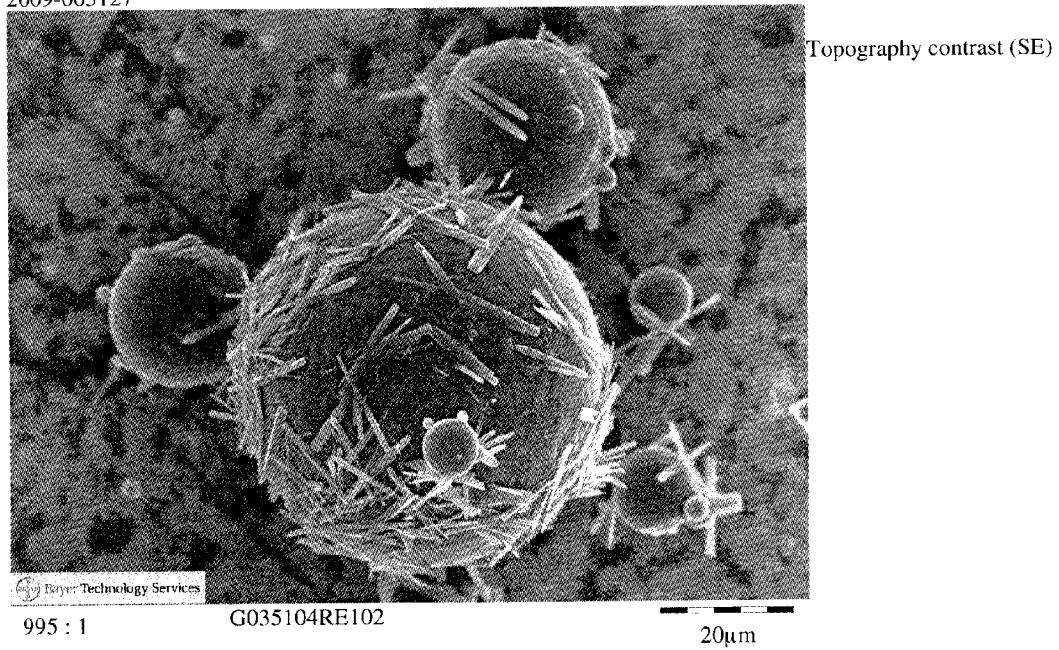

COMPOSITION COMPRISING INSECTICIDE-WAX PARTICLES

CROSS-REFERENCE TO RELATED APPLICATIONS

This application claims priority to EP 10195657.1, filed Dec. 17, 2010, U.S. Provisional Patent Application 61/442,445 filed Feb. 14, 2011 and EP 11162403.7, filed Apr. 14, 2011, the contents of each are hereby incorporated by reference in their entirety.

FIELD OF THE INVENTION

The present invention relates to compositions for pest control, more particularly insecticides, to a process for preparing them, and to the use of such formulations for sustained control of animal pests (arthropods) on various surfaces. The present invention further relates to active ingredient-wax particles in which at least one active insecticidal ingredient is dispersed in wax.

BACKGROUND OF THE INVENTION

The control of arthropods inside and outside buildings and houses is necessary for a variety of reasons. In countries where arthropods such as insects or arachnids transmit diseases to humans and animals, an example being malaria, there is a great need to provide the inhabitants with effective and long-term protection. Furthermore, considerations of hygiene and of structural engineering dictate that animal pests should be prevented from gaining access to buildings, spreading and residing in buildings, and infesting wood or other materials. For this reason, a large number of control products and techniques have already been developed. The most common method of control is the application of active insecticidal ingredients in aqueous solutions for atomizing or spraying. Regardless of the active ingredient used, the efficacy of the spray coating is also heavily dependent on the physicochemical properties of the surface sprayed. The duration of effect of the spray coating is greatly impaired and reduced in particular on porous surfaces and more particularly on alkaline porous surfaces (also referred to as aggressive surfaces) such as concrete, render, stone/brickwork, timber (treated and untreated), ceramic, straw or thatch, chalky, limey, gypsiferous, cement-containing and loamy surfaces. As a result, in the case of the control of malaria mosquitoes within buildings, for example, there are short duration effects of 6 months at most.

BRIEF SUMMARY OF THE INVENTION

In pest control outside the house, it is the walls of the house, the soil, plants and turf areas that are treated. Here, not only the surface properties (porosity, pH) but additionally the effects of temperature, UV and rain mean that the active ingredients used rapidly lose their activity.

Systemic active agrochemical ingredients are typically formulated as an emulsifiable concentrate (EC), a soluble liquid (SL) and/or an oil-based suspension concentrate (OD). In an EC or SL formulation, the active ingredient is in dissolved form, while in an OD formulation it is present as a solid. Also technically possible in general is a suspension concentrate (SC) or water-dispersible granules (WG). While only suspension concentrates are described below, the reference also comprehends other modes of formulation in which the active ingredient is present in a water-dispersible form.

The particle size of active ingredient in suspension concentrates comprising micronized crystals of active ingredient which are formulated with auxiliaries is typically around 1 to 3 µm. It was known that active ingredient particles with a large particle size are able to produce an improved biological action. The provision of larger active ingredient particles, however, has economic drawbacks. Instead of larger active ingredient particles, it is also possible to use particles consisting of inert carrier particles coated with active ingredient. In that case the active ingredients are generally obtained by the spraying of solutions containing active ingredient onto the carrier particles. Producing active ingredient forms of this kind, however, is technically complex and expensive.

Waxes micronized by spray solidification have already been used for a long time in a diversity of applications, such as in polishes, for example.

Waxes, moreover, are frequently used as coatings in order to modify the surface of granules, in sectors which include those of crop protection and pest control.

WO 00/49107 discloses mixtures of plant treatment agents with one or more waxes. The use of these mixtures as surface treatment products is not mentioned in the document. The purpose of mixing with wax is to reduce the volatility of active ingredients, to reduce user toxicity, to reduce the phytotoxic effects of the active ingredients, to increase the reliability of action, to raise the rain resistance of the formulation film, and to achieve slow release of the active ingredient. In accordance with this teaching, therefore, it is possible either to reduce the quantities of active ingredient or to extend the intervals between spraying. The mixtures are produced by direct mixing of active ingredient and wax, by melt combination in a mixer, or by dispersing of the active ingredient in a wax dispersion with addition of auxiliaries, with wax depositing in finely distributed form on the active ingredient. A preferred alternative for producing the mixtures described is to treat a ready-made commercial plant treatment emulsifiable concentrate with wax or to add wax, preferably in the form of a wax dispersion, to the emulsifiable concentrate.

WO 95/34200 describes compositions which are borne into a variety of forms and which are composed of two or more different waxes which differ in water solubility, and of active crop protection ingredients. These compositions are produced by different methods such as melt combination, spray solidification or extrusion. Among the forms the mixtures take are spherical or hemispherical grains, the particle size of which is not disclosed, and they are used fundamentally in solid form, but not as a dispersion or suspension. The purpose of mixing with wax is to retard the release of the active ingredient.

WO 97/35476 describes the incorporation of aromatic compounds such as, for example, cinnamaldehyde or coniferylaldehyde into wax in the form of microcapsules, by encapsulation in an aqueous emulsion, and the use thereof in various formulations for the control of insect pests or as insect traps.

WO 1995/028835 discloses a process for producing a pesticide-containing wax matrix by extrusion, by treating a plurality of waxes having different properties, and a pesticide, using a multi-screw extruder. As a result of the different properties of the waxes used, which are mixed homogeneously, the pesticide can be released in a controlled way. Here, the aim of the process is the delayed release of the active ingredient.

DE-A 1207144 discloses solid fumigants comprising dimethyl chlorovinyl phosphate as active ingredient, said active ingredient being present in dispersion in a carrier, namely montan wax, hydrogenated cotton seed oil or dibutyl phthalate. The solid mixtures obtained are provided in the form of cylinders, tapes or the like, and so the active ingredient, following volatilization from the surface of the preparation, comes into contact with the moisture in the air. According to this teaching, the aim is to achieve a long-lasting and extremely uniform effect of the volatile active ingredient.

Similar solid fumigants are also known from DE-A 2023367.

U.S. Pat. No. 4,882,167 describes controlled-release compositions comprising a hydrophobic carbohydrate polymer, a wax and a biologically active agent, a pesticide inter alia, which are obtained by direct dry compression of the ingredients to form a tablet or implants. The aim is to achieve uniform controlled release of the active ingredient.

U.S. Pat. No. 6,001,346 discloses solid formulations comprising sprayable or solid biodegradable waxes as carriers for insect pheromones. The composition may also comprise insecticides as secondary bioactive agents. The composition is produced by a melt combination of the components and shaping to form plates or granules, or direct emulsification in water. The composition exhibits controlled and uniform release of the pheromone.

US 2008/0003197 discloses similar pheromone compositions, in forms which include aqueous emulsions or dispersions. As a secondary bioactive ingredient, these compositions may also comprise an insecticide.

WO 03/045877 describes microgranules which comprise a combination of fertilizer and crop protection agent—a pesticide, for example. They comprise a co-adjuvant, which among other compounds may be a wax, in an amount of up to 1% by weight. The particle size of the microgranules is 0.1 to 2 mm (100 to 2000 µm).

EP-A 0 021 477 discloses compositions comprising a solid oil or wax and a systemic pesticide, typically in the form of pellets or granules, the pesticide being present in dispersion in the oil/wax, in inclusions, and the diameter of the inclusions being $10^{-8}$ to $10^{-5}$ m (0.0001 to 0.1 µm). The wax-pesticide particles are added to a liquid mixture of dispersant and wax by addition of the pesticide (with stirring), this system is emulsified and then divided into droplets, which then solidify in a receiving zone (spray solidification).

EP-A 0 721 734 (WO 95/09532) describes a composition which is produced by melting and features delayed release, comprising a hydrophobic substance having a melting point of more than 50° C., and an oil-absorbing substance, and also a pesticide. In general the composition is produced by extrusion, giving granules having a particle size of 0.8 to 2 mm (800 to 2000 µm) in size.

WO 2010/031508, from the applicant, discloses insecticidal fumigants which are produced using aqueous dispersions. These dispersions comprise wax particles which incorporate an insecticide, through melting and spray solidification or hot emulsification. The particle size of the insecticide-wax particles is 0.01 to 100 µm, preferably 0.1 to 30 µm. These aqueous dispersions preferably comprise an evaporation inhibitor and are processed into exclusively burnable fumigants, known as coils. The purpose of incorporating the insecticide in the form of wax-insecticide particles is to improve the shelf life of the coils. A range of active ingredients, in lists, are said to be suitable, but the examples provide explicit disclosure only of transfluthrin. The use of the aqueous dispersions themselves as an insecticidal formulation is likewise not disclosed.

WO 2006/117158 discloses the use of aqueous wax dispersions for impregnating lignocellulosic materials, preferably wood. The wax particles have a diameter of less than 500 nm (0.5 µm). The dispersion or the wax particles may also comprise effect substances or active ingredients, such as colorants, UV absorbers, antioxidants, stabilizers, and active ingredients for protecting wood or lignoscellulosic material from infestation by harmful organisms, especially wood-destroying insects. Among the active ingredients disclosed there are a series of insecticides. The examples do not contain any description of wax particles comprising an active insecticidal ingredient. No production method is specified for insecticide-containing wax particles. The wax dispersions described in the examples are in each case produced by dispersing or emulsifying wax in water at 95° C.

JP-A 7242502 discloses an agrochemical composition with delayed release of the active ingredient, in which the active ingredient is tabletted or melted together with a wax and a water-insoluble mineral oil. The product is subsequently brought to a particle size of 0.1 to 0.5 mm (100 to 500 µm) and used directly.

JP-A 5305226 describes an agrochemical composition with delayed release of the active ingredient nitenpyram, in which carnauba wax is melted at 90° C. and admixed with nitenpyram. A wetting agent is added in order to disperse nitenpyram homogeneously in the wax. The composition obtained is cooled in a spray dryer and granulated to 50-200 p.m. In the case of this laid-open specification, in contrast to the present invention, the objective is a contrary one (delayed release, in contrast to the present invention, where the focus is on rapid bioavailability). As a result of the necessary wetting agent in the case of JP-A 5305226, the crystallization of the active ingredients on the surface of the wax particles, which is a characteristic of the present composition of the invention, is prevented. The wax particle size in the present composition is smaller, at 1 to 40 µm, than that of JP-A 5305226.

JP-A 2000351705 describes a mixture of montan ester wax and montan wax, an inorganic carrier such as calcium carbonate, for example, and an active agrochemical ingredient, in the form of granules.

There is an ongoing need to improve the activity of the products under the difficult conditions identified above. Through longer-lasting protection it is possible to minimize the exposure of the user, the inhabitants, the pets and the environment, since active ingredient need be applied less frequently.

BRIEF DESCRIPTION OF THE FIGURES

FIG. 1: Micrograph of the surface of an active ingredient-wax particle

DETAILED DESCRIPTION

The object on which the present invention was based was therefore that of providing new, improved insecticidal compositions which offer long-lasting protection from insects when the compositions are applied to surfaces. They are to be suitable more particularly for porous and/or alkaline surfaces and to be resistant to environmental effects such as high/low/fluctuating temperatures, UV radiation and rain.

The object of the invention was, moreover, to provide insecticidal compositions which ensure rapid bioavailability and outstanding and long-lasting activity with a lower amount employed. Furthermore, the compositions ought to exhibit high stability on aggressive substrates.

This object is achieved through the insecticidal compositions of the invention. Compositions of the invention are, for example, aqueous suspension concentrates or spray mixtures produced from them, which generally have a range of advantageous properties. For instance, the compositions of the invention are solvent-free. Furthermore, they are easy to handle and to produce. Spray mixtures that can be used in accordance with the invention may be prepared by diluting a concentrate in water or by mixing different preliminary solutions immediately prior to spraying (tank mix application). Compositions of the invention may also be ready-to-use (RTU) formulations. A further advantage is shown in the rapid bioavailability of the insecticidal composition of the invention.

The insecticidal composition of the invention comprises
  at least one active insecticidal ingredient,
  wax having a melting point of 50 to 160° C. under standard conditions,
  water and
  customary additives and/or auxiliaries,
  wherein
  the active insecticidal ingredient or ingredients is or are dispersed in the wax, and the insecticide-containing wax is present in the composition in the form of particles, the particles having a particle size (d50, determined after dispersion in the water phase by laser diffraction) of 5 to 40 μm, and crystals of the active ingredient or ingredients being present at the surface of the particles (visible when viewed with a microscope).

It has surprisingly been found that the compositions of the invention, following application to a surface, optionally after dilution with water, have a rapid bioavailability and an improved long-term biological action in comparison to the prior art. This applies particularly in the case of the treatment of porous surfaces, and especially alkaline porous surfaces, such as concrete, render, stone/brickwork, timber (treated and untreated), ceramic, straw or thatch, chalky, limey, gypsiferous, cement-containing and loamy surfaces. The action is substantially unaffected in the case of application to nonporous surfaces.

Furthermore, it has surprisingly been found that the durability of the spray coatings obtained by using the aqueous suspension concentrates of the invention is significantly better, even under the influence of high/low/fluctuating temperatures, rain and UV irradiation, than that of known coatings.

FIG. 1 shows a micrograph (scanning electron microscope ESEM Quanta 400 from FEI Company Deutschland GmbH) of the surface of active ingredient-wax particles according to the invention. The active ingredient is deltamethrin. The active ingredient crystals at the surface of the particles are clearly apparent.

The compositions of the invention preferably comprise one or more active insecticidal ingredients selected from those below. The active ingredients, given in this description by their common name, are known from, for example, The Pesticide Manual, 14th Edition, British Crop Protection Council 2006, and from the website www.alanwood.net/pesticides.

(1) acetylcholinesterase (AChE) inhibitors, such as, for example,
carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or
organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion;

(2) GABA-gated chloride channel antagonists, such as, for example,
organochlorines, for example chlordane and endosulfan (alpha-); or
fiproles (phenylpyrazoles), for example ethiprole, fipronil, pyrafluprole and pyriprole;

(3) sodium channel modulators/voltage-dependent sodium channel blockers, such as, for example,
pyrethroids, for example acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, fluvalinate (tau-), halfenprox, imiprothrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; or
DDT; or methoxychlor;

(4) nicotinergic acetylcholine receptor agonists, such as, for example
neonicotinoids, for example acetamiprid, clothianidin, dinotefuran, imidacloprid, nitenpyram, thiacloprid, thiamethoxam; or
nicotine;

(5) allosteric acetylcholine receptor modulators (agonists), such as, for example
spinosyns, for example spinetoram and spinosad;

(6) chloride channel activators, such as, for example
avermectins/milbemycins, for example abamectin, emamectin benzoate, lepimectin and milbemectin;

(7) juvenile hormone analogues, for example hydroprene, kinoprene, methoprene; or fenoxycarb; pyriproxyfen;

(8) active compounds with unknown or non-specific mechanisms of action, such as, for example
fumigants, for example methyl bromide and other alkyl halides; or
chloropicrin; sulphuryl fluoride; borax; tartar emetic;

(9) selective antifeedants, for example pymetrozine; or flonicamid;

(10) mite growth inhibitors, for example clofentezine, diflovidazin, hexythiazox,
etoxazole;

(11) microbial disruptors of the insect gut membrane, such as, for example, *Bacillus thuringiensis* subspecies *israelensis*, *Bacillus sphaericus*, *Bacillus thuringiensis* subspecies *akawai*, *Bacillus thuringiensis* subspecies *kurstaki*, *Bacillus thuringiensis* subspecies *tenebrionis*, and BT plant proteins, for example Cry1Ab, Cry1Ac, Cry1Fa, Cry2Ab, mCry3A, Cry3Ab, Cry3Bb, Cry34/35Ab1;

(12) oxidative phosphorylation inhibitors, ATP disruptors, such as, for example, diafenthiuron; or
organotin compounds, for example azocyclotin, cyhexatin, fenbutatin oxide; or
propargite; tetradifon;

(13) oxidative phoshorylation decouplers acting by interrupting the H proton gradient, such as, for example, chlorfenapyr and DNOC;

(14) nicotinergic acetylcholine receptor antagonists, such as, for example, bensultap, cartap (hydrochloride), thiocylam, and thiosultap (sodium);

(15) chitin biosynthesis inhibitors, type 0, such as, for example, benzoylureas, for example bistrifluron, chlorfluazuron, diflubenzuron, flucycloxuron, flufenoxuron, hexaflumuron, lufenuron, novaluron, noviflumuron, teflubenzuron and triflumuron;

(16) chitin biosynthesis inhibitors, type 1, such as, for example, buprofezin;

(17) moulting disruptors, such as, for example, cyromazine;

(18) ecdysone agonists/disruptors, such as, for example, diacylhydrazines, for example chromafenozide, halofenozide, methoxyfenozide and tebufenozide;

(19) octopaminergic agonists, such as, for example, amitraz;

(20) complex-III electron transport inhibitors, such as, for example, hydramethylnone; acequinocyl; fluacrypyrim;

(21) complex-I electron transport inhibitors, for example from the group of the METI acaricides, for example fenazaquin, fenpyroximate, pyrimidifen, pyridaben, tebufenpyrad, tolfenpyrack or
rotenone (Derris);

(22) voltage-dependent sodium channel blockers, for example indoxacarb; metaflumizone;

(23) inhibitors of acetyl-CoA carboxylase, such as, for example, tetronic acid derivatives, for example spirodiclofen and spiromesifen; or tetramic acid derivatives, for example spirotetramat;

(24) complex-IV electron transport inhibitors, such as, for example, phosphines, for example aluminium phosphide, calcium phosphide, phosphine, zinc phosphide; or cyanide;

(25) complex-II electron transport inhibitors, such as, for example, cyenopyrafen; or

(26) ryanodine receptor effectors, such as, for example, diamides, for example, chlorantraniliprole (Rynaxypyr), cyantraniliprole (Cyazypyr) and flubendiamide.

Further active compounds with an unknown mechanism of action, such as, for example, azadirachtin, amidoflumet, benzoximate, bifenazate, chinomethionat, cryolite, cyflumetofen, dicofol, flufenerim, pyridalyl and pyrifluquinazon; or the known active compounds below: 4-{[(6-bromopyrid-3-yl)methyl](2-fluoro ethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2-fluoroethyl)amino}furan-2(5H)-one (known from WO 2007/115644), 4-{[(6-chloropyrid-3-yl)methyl](2-fluoro ethyl)amino}furan-2(5H)-one (known from WO 2007/115644), 4-{[(6-chloropyrid-3-yl)methyl](2,2-difluoroethyl)amino}furan-2(5H)-one (known from WO 2007/115644), 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [(6-chloropyridin-3-yl)methyl](methyl)oxido-$\lambda^4$-sulphanylidenecyanamide (known from WO 2007/149134), [1-(6-chloropyridin-3-yl)ethyl](methyl)oxido-$\lambda^4$-sulphanylidenecyanamide (known from WO 2007/149134) and its diastereomers (A) and (B)

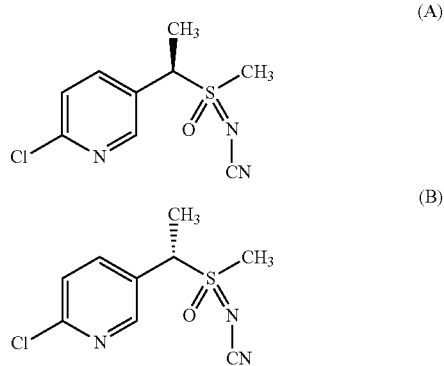

(also known from WO 2007/149134), [(6-trifluoromethylpyridin-3-yl)methyl](methyl)oxido-$\lambda^4$-sulphanylidenecyanamide (known from WO 2007/095229), sulfoxaflor (also known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911) and 1-{2,4-dimethyl-5-[(2,2,2-trifluoroethyl)sulphinyl]phenyl}-3-(trifluoromethyl)-1H-1,2,4-triazole (known from WO 1999/55668).

The compositions of the invention comprise preferably
at least one insecticide selected from deltamethrin, beta-cyfluthrin, cyfluthrin, cypermethrin, alpha-cypermethrin, bendiocarb, bifenthrin, permethrin, pyrethrum, lambda-cyhalothrin, gamma-cyhalothrin, etofenprox, pyrethrum, particularly natural pyrethrum, indoxacarb, carbaryl, fipronil, metaflumizone, azadirachtin, flubendiamide, chlorantraniliprole, boric acid, borax, imidacloprid, clothianidin, dinotefuran and acetamiprid, fenpyroximate, fipronil or tolfenpyrad, spinosad.

The compositions of the invention comprise more preferably
at least one insecticide selected from deltamethrin, beta-cyfluthrin, cyfluthrin, lambda-cyhalothrin, bendiocarb, natural pyrethrum or fipronil.

Very preferably in accordance with the invention deltamethrin is one of the insecticides present in the composition.

WO 2010/031508 from the applicant discloses insecticidal fumigants and describes, in claim 7 and in the examples, an aqueous dispersion comprising wax particles, insecticide and evaporation inhibitor, with a wax particle size of 0.01 to 100 μm. This aqueous dispersion is used to produce the fumigant, and results in an increase in the shelf life of the fumigants. The present insecticidal composition differs from the aqueous dispersion preferably in that there is no evaporation inhibitor present (as defined in WO 2010/031508). In a further preferred subject of the present invention, the insecticidal composition of the invention is not used for preparing insecticidal fumigant. In contrast to the aqueous dispersions specifically evidenced with examples in WO2010/031508, the active insecticidal ingredient used in accordance with the invention is preferably not transfluthrin Preferred compositions of the invention are those with a single active insecticidal ingredient, more particularly with deltamethrin.

Inert carriers used are, in accordance with the invention, customary inert carriers having a melting point of between 50 and 160° C., preferably between 60 and 140° C. and more preferably between 70 and 120° C. under standard conditions. In this description they are referred to as wax.

Waxes contemplated preferentially are plant waxes such as, for example, cotton wax, carnauba wax, candelilla wax, japan wax, sugarcane wax; animal waxes such as, for example, beeswax, wool wax, shellac wax; mineral waxes such as, for example, ceresin, ozokerite and montan wax. Furthermore, chemically modified waxes may be used in accordance with the invention, such as, for example, hydrogenated jojoba waxes, montan ester wax and fully synthetic waxes such as polyalkylene waxes, polyethylene glycol waxes, amide waxes, Fischer-Tropsch paraffin waxes and fluorocarbon waxes.

Further suitable waxes in accordance with the invention are hydrogenated and unhydrogenated fats, examples being triglycerides or fatty acids such as, for example, stearin, coconut oil or hydrogenated oils such as, for example, hydrogenated palm oil or hydrogenated castor oil.

In accordance with the invention, the waxes can be used in macrocrystalline, microcrystalline or amorphous form.

Used with particular preference as wax in accordance with the invention are carnauba wax and montan wax. Carnauba wax is especially preferred.

Apart from wax and insecticide(s), as defined above, the insecticide-wax particles of the invention preferably comprise no further components. In particular they preferably comprise no pheromones, no carbohydrate polymers, no oil-absorbing substances (in particular no starch, starch derivatives, cellulose, amorphous silica, clay, talc), no inorganic carriers, no evaporation inhibitors, no fertilizers, and no mineral oil that is liquid under standard conditions.

Besides the wax-insecticide particles indicated above, the compositions of the invention comprise one or more customary auxiliaries and/or additives from the groups of the dispersing assistants, release agents (anti-caking agents), frost preventatives, foam inhibitors, preservatives, antioxidants, spreaders and/or colorants. The compositions of the invention may further comprise a thickener (including, where appropriate, a thickening activator), one or more acids or bases in an amount such as to set a specific pH for the composition or to activate thickeners, and also further components for optimizing the performance properties of the formulation.

Suitable thickeners include all substances which can typically be employed for this purpose in agrochemical products and which function as thickeners. Those preferred are inorganic particles, such as carbonates, silicates and oxides, and also organic substances, such as urea-formaldehyde condensates. Mention may further be made, by way of example, of kaolin, rutile, silicon dioxide, highly disperse silica, silica gels, and also natural and synthetic silicates, and talc. As thickeners it is possible, furthermore, to use synthetic thickeners such as polyacrylate thickeners (e.g. Carbopol® and Pemulen® thickeners from Lubrizol, Cleveland, USA), biological thickeners (e.g. Kelzan® S, xanthan gum, or other hydrocolloids from CP Kelco, Atlanta, USA) and inorganic thickeners (e.g. phyllosilicates such as kaolin, montmorillonite and laponite). Particularly suitable in accordance with the invention are biological thickeners such as, for example, heteropolysaccharides, for example anionic heteropolysaccharides such as xanthan gum. Particular preference is given to xanthan gum (Kelzan® S).

As release agents (anti-caking agents), which are intended to prevent agglomeration of ingredients in the composition, typical release agents are employed. Preference is given in accordance with the invention to using fumed silica (amorphous pyrogenic silicon dioxide, e.g. Aerosil®, from Evonik Industries).

Suitable acids or bases for pH adjustment are typical organic and inorganic acids and bases. As a base it is preferred to use weak inorganic bases such as aqueous ammonia, while as acids it is preferred to use weak organic acid such as citric acid, for example. These agents are added to the composition in suitable amounts in order to set the desired pH. The pH (at RT) of the composition is typically 3-7.

Suitable foam inhibitors include all of the substances which can be used for this purpose in agrochemical products. Silicone oils and magnesium stearate are preferred. Particularly suitable in the context of the invention is Rhodorsil® (from Bluestar Silicones), a polydimethylsiloxane, which is offered in aqueous emulsion.

In accordance with the invention, dispersing assistants are optionally also used. Contemplated for this purpose are, for example, customary emulsifiers, especially customary wax emulsifiers. Particular mention here is given to Wax Emulsifier 4106® (from Clariant), a mixture of alkyl ethoxylates. This is a nonionic emulsifier, which is used with preference in accordance with the invention.

As dispersing assistants it is also possible to use surfactants. Suitable nonionic surfactants, in addition to those specified above, include all compounds of this type that can typically be used in agrochemical products. Those that may be mentioned with preference are polyethylene oxide-polypropylene oxide block copolymers, polyethylene glycol ethers of linear alcohols, reaction products of fatty acids with ethylene oxide and/or propylene oxide, and also polyvinyl alcohol, polyvinyl pyrrolidone, copolymers of polyvinyl alcohol and polyvinyl pyrrolidone, copolymers of polyvinyl acetate and polyvinyl pyrrolidone, and copolymers of (meth)acrylic acid and (meth)acrylic esters, and also alkyl ethoxylates and alkylaryl ethoxylates, which where appropriate may be phosphatized and where appropriate may be neutralized with bases, and also polyoxyamine derivates and nonylphenol ethoxylates.

Anionic surfactants contemplated include all substances of this type that can typically be employed in agrochemical products. Preference is given to alkali metal salts and alkaline earth metal salts of alkylsulphonic acids or alkylarylsulphonic acids.

Another preferred group of anionic surfactants or dispersing assistants are salts of polystyrenesulphonic acids, salts of polyvinylsulphonic acids, salts of naphthalenesulphonic-formaldehyde condensation products, salts of condensation products of naphthalenesulphonic acid, phenolsulphonic acid and formaldehyde, and salts of lignosulphonic acid.

Preference is given to nonionic surfactants selected from polyethylene glycol ethers of linear alcohols, reaction products of fatty acids with ethylene oxide or propylene oxide.

Frost preventatives contemplated include all substances of this type that can commonly be employed in agrochemical products. Preference is given to urea, glycerol or propylene glycol. Another preferred group of frost preventatives are additives from the group of the polyglycerols or polyglycerol derivatives. In accordance with the invention, 1,2-propylene glycol is employed with particular preference.

Preservatives contemplated include all substances that can commonly be employed for this purpose in agrochemical products of this type. Examples include Preventol® (mixture of 2 isothiazolones, from Lanxess AG) and Proxel® (1,2-benzisothiazol-3-one, from Arch Chemicals, Inc.).

Suitable antioxidants include all substances which can typically be used for this purpose in agrochemical products. Preference is given to butylated hydroxytoluene (2,6-di-t-butyl-4-methyl-phenol, BHT).

Suitable spreaders are all substances which can typically be employed for this purpose in agrochemical products. Preference is given to polyether polysiloxanes or organically modified polysiloxanes.

Colorants contemplated include all substances that can typically be employed for this purpose in agrochemical products. Examples include titanium dioxide, pigmentary carbon black, zinc oxide and blue pigments, and also Permanent Red FGR.

The fraction of active ingredient in suspension concentrates of the invention may be varied within a wide range. All % figures in this description are % by weight, unless indicated otherwise.

In suspension concentrates of the invention which are diluted with water prior to use, the amount of active ingredient is typically 0.5% to 5% by weight, preferably 0.5% to 2.5% by weight, e.g. about 1% by weight based on the suspension concentrate.

The water fraction in suspension concentrates is, in accordance with the invention, about 65% to 90%, preferably 70% to 85%, based on the suspension concentrate.

The fraction of wax in the suspension concentrates is, in accordance with the invention, about 2% to 13%, preferably about 3% to 11.5% and more preferably 4% to 10%, based on the suspension concentrate.

The auxiliaries and additives make up the rest of the suspension concentrate.

In general the suspension concentrates, for the purpose of preparing an application-ready formulation, are diluted with (i.e. the spraying liquor) water in a ratio of 1:50 to 1:500, depending on the desired concentration of active ingredient.

In the case of formulations diluted for use (i.e. the spraying liquor), the active ingredient fraction is generally, depending on the active ingredient, between 0.00025% and 1% by weight, preferably between 0.00125% and 0.5% by weight, more preferably between 0.0025% and 0.25% by weight, based on the ready-to-use composition as a whole.

Furthermore, when the compositions of the invention are used in their standard commercial formulations and also in the forms of application that are prepared from these formulations, they may be present in a mixture with synergists. Synergists are compounds which boost the action of the active ingredients present in the compositions of the invention, without the synergist added necessarily being actively effective itself.

Application takes place in a customary way which is appropriate to the application forms.

Suspension concentrates of the invention are produced by mixing the components with one another in the particular desired proportions. The sequence in which the ingredients are combined with one another is arbitrary, although the thickener is typically added last. It is advantageous to use the solid components, apart from the active ingredient-wax particles of the invention, in finely ground form. An alternative option is to take the suspension formed by combining the ingredients (except for the active ingredient-wax particles, which have the average particle size specified below) and subject it first to a coarse grinding operation and then to a fine grinding operation, so that the average particle size is, for example, below 5 μm.

The temperatures during the production of the composition of the invention may be varied within a certain range. Suitable temperatures are between 10° C. and 60° C., preferably between 15° C. and 40° C. Typical mixing and grinding equipment is suitable for producing the composition, of the kind used for producing agrochemical formulations.

The active ingredient-containing wax particles of the invention are obtained by spray solidification. They are coarse, in other words having an average particle size d50 of 5-40 μm, preferably 10 to 35 μm, more preferably about 15 μm (as determined after dispersion in the water phase, by laser diffraction with a Malvern Mastersizer S). In this case first of all a melt is produced from the wax, which is solid under standard conditions at room temperature. Then the active ingredient is incorporated uniformly into the melt, using, for example, a magnetic stirrer. The resultant mixture is referred to in the present description as spraying solution. In accordance with the invention, this spraying solution is atomized from the reservoir into a controlled environment, with the aid, for example, of a pump, through a die having a suitably selected diameter. The reservoir, the pump, the die and all the lines which come into contact with the spraying solution are heated to at least 90° C. The spraying solution is atomized with a spraying gas pressure of about 0.8 bar into a substantially cold environment, in a spraying tower, for example. The temperature of this environment is −10 to 40° C., preferably 0 to 25° C., more preferably 15 to 20° C. As a result of the rapid cooling on entry into the cold spraying tower, the sprayed droplets of the spraying solution solidify very rapidly, and solid particles are obtained which are approximately spherical in shape. The atomizer die is selected such that the resultant solid active ingredient-wax particles have a particle size d50 of preferably about 10 to 35 μm. The particles obtained are taken from the spraying tower in a usual way, by means of a cyclone, for example. Within the particles the active ingredient is present in uniform distribution. A further subject of the present invention is therefore a process for preparing the active ingredient-wax particles of the invention by means of the spray solidification described above.

When the resultant active ingredient-wax particles are subsequently incorporated, in accordance with the invention, into an aqueous suspension, the active ingredient diffuses from the interior of the particles to the surface (carrier/water interface) where it crystallizes. Particles are then obtained which on their surface have crystals which are clearly visible under the microscope—FIG. 1: (scanning electron microscope ESEM Quanta 400 from FEI Company Deutschland GmbH). In other words, when the particles are introduced into water, there is a phase transition from molecularly disperse or amorphous to crystalline, and a migration of the active ingredient from the particle interior, and then accumulation of active ingredient at the surface. It is thought that the specific structure of the particles of the invention is the cause of the enhanced effect. This is the case when the concentration of active ingredient, preferably of deltamethrin, in the wax is between 20% and 30% by weight.

The active ingredients of the invention combine good crop tolerance, favourable homeotherm toxicity and good environmental friendliness with a capacity to control animal pests, more particularly insects, arachnids, helminths, nematodes and molluscs, which are prevalent in agriculture, in horticulture, in animal husbandry, in forests, in gardens and in leisure facilities, in storehouse protection and materials protection, and in the hygiene segment. They are active against species with normal sensitivity and resistance species, and also against some or all stages of development.

A further embodiment of the invention is an insecticidal compositions which can be prepared (preferably is prepared) by the preparation process stated in this application.

The pests referred to above include the following:

From the order of the Anoplura (Phthiraptera) e.g. *Damalinia* spp., *Haematopinus* spp., *Linognathus* spp., *Pediculus* spp., *Trichodectes* spp.

From the class of the Arachnida e.g. *Acarus* spp., *Aceria sheldoni*, *Aculops* spp., *Aculus* spp., *Amblyomma* spp., Amphi*tetranychus viennensis*, *Argas* spp., *Boophilus* spp., *Brevipalpus* spp., *Bryobia praetiosa*, *Centruroides* spp., *Chorioptes* spp., *Dermacentor* spp., *Dermanyssus gallinae*, *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus mactans*, *Loxosceles* spp., *Metatetranychus* spp., *Nuphersa* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tenenaria* spp., *Tetranychus* spp., *Vaejovis* spp., *Vasates lycopersici*.

From the class of the Bivalva e.g. *Dreissena* spp.

From the order of the Chilopoda e.g. *Geophilus* spp., *Scutigera* spp.

From the order of the Coleoptera e.g. *Acalymma vittatum*, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Psylliodes* spp., *Ptinus* spp., *Rhizobius ventralis*, *Rhizopertha dominica*, *Sitophilus* spp., *Sphenophorus* spp., *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Collembola e.g. *Onychiurus armatus*.

From the order of the Diplopoda e.g. *Blaniulus guttulatus*.

From the order of the Diptera e.g. *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Cochliomyia* spp., *Contarinia* spp., *Cordylobia anthropophaga*, *Culex* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit*, *Pegomyia* spp., *Phorbia* spp., *Prodiplosis* spp., *Psila rosae*, *Rhagoletis* spp., *Stomoxys* spp., *Tabanus* spp., *Tannia* spp., *Tetanops* spp., *Tipula* spp.

From the class of the Gastropoda e.g. *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

From the order of the Heteroptera e.g. *Anasa tristis*, *Antestiopsis* spp., *Blissus* spp., *Boisea* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

From the order of the Homoptera e.g. *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma pini*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*,

*Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Hymenoptera e.g. *Acromyrmex* spp., *Athalia* spp., *Atta* spp., *Camponotus* spp., *Diprion* spp., *Hoplocampa* spp., *Lasius* spp., *Linepithema* spp., *Monomorium pharaonis, Paratrechina* spp., *Pheidole* spp., *Plagiolepis* spp., *Solenopsis* spp., *Tapinoma* spp., *Tetramorium* spp., *Vespa* spp., *Vespula* spp.

From the order of the Isopoda e.g. *Armadillidium vulgare, Oniscus asellus, Porcellio scaber.*

From the order of the Isoptera e.g. *Coptotermes* spp., *Cornitermes cumulans, Cryptotermes* spp., *Incisitermes* spp., *Microtermes obesi, Odontotermes* spp., *Reticulitermes* spp, From the order of the Lepidoptera e.g. *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia kuehniella, Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Tineola* spp., *Thermesia gemmatalis, Tinea pellionella, Tineola bisselliella, Tortrix* spp., *Trichoplusia* spp., *Tuta absoluta, Virachola* spp.

From the order of the Orthoptera e.g. *Acheta domesticus, Blatta orientalis, Blattella germanica, Dichroplus* spp., *Gryllotalpa* spp., *Leucophaea maderae, Locusta* spp., *Melanoplus* spp., *Periplaneta americana, Schistocerca gregaria.*

From the order of the Siphonaptera e.g. *Ceratophyllus* spp., *Ctenocephalides* spp., *Xenopsylla cheopis.*

From the order of the Symphyla e.g. *Scutigerella* spp.

From the order of the Thysanoptera e.g. *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura e.g. *Lepisma saccharina, Thermobia* spp.

The plant-parasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

The formulations of the invention can be used with preference for eliminating harmful or nuisance arthropods, especially arachnids and insets such as sucking or biting insects.

The particularly preferred arachnids include scorpions, spiders, mites and ticks.

The particularly preferred sucking insects include essentially the mosquitoes, moth gnats, gnats, buffalo gnats, stinging flies, tsetse flies, horseflies, true flies, meat flies, myiasis-causing flies, bugs and sand fleas.

The particularly preferred biting insects include essentially cockroaches, beetles, termites, ants, wasps and moth larvae.

With very particular preference the materials according to the invention are used against spiders, mosquitoes, flies, bugs, cockroaches, ants and beetles.

Where the compositions of the invention are not in ready-to-use form (e.g. as aqueous suspension concentrate), they are first diluted in water for their use as intended. Dilution takes place to an extent such that the active ingredient content ensures a sufficient insecticidal action at the intended application rate. Dilution produces compositions which correspond to the ready-to-use compositions specified above.

The diluted spraying solution (also referred to in the application as spraying liquor) can be sprayed in any usual way, using manually operated or electrical sprayers, for example.

One particularly preferred embodiment of the invention relates, furthermore, to a spraying liquor comprising an insecticidal composition of the invention, the active insecticidal ingredient in the insecticidal composition being at least one of the following active insecticidal ingredients:

deltamethrin, with deltamethrin being present in a concentration of 10 to 240 mg per liter of spraying liquor, preferably of 20 to 125 mg per liter of spraying liquor, or beta-cyfluthrin, with beta-cyfluthrin being present in a concentration of 20 to 125 mg per liter of spraying liquor, or cyfluthrin, with cyfluthrin being present in a concentration of 100 to 300 mg per liter of spraying liquor, or lambda-cyhalothrin, with lambda-cyhalothrin being present in a concentration of 20 to 125 mg per liter of spraying liquor, or bendiocarb, with bendiocarb being present in a concentration of 1000 to 2000 mg per liter of spraying liquor, or nat pyrethrum, with nat pyrethrum being present in a concentration of 200 to 1000 mg per liter of spraying liquor, or fipronil, with fipronil being present in a concentration of 20 to 200 mg per liter of spraying liquor.

A further subject of the invention relates to the use of an insecticidal composition of the invention for preparing the spraying liquor of the invention.

A further subject of the invention pertains to the use of an insecticidal composition of the invention and/or of an active ingredient-wax particle of the invention or of a spraying liquor of the invention for pest control and more particularly for freeing surfaces from pest infestation and/or for protecting surfaces from pest infestation.

An active ingredient here is applied generally in a concentration per unit area of 0.05 to 1000 mg/m², preferably at a concentration of 0.05 to 500 mg/m², more preferably at a concentration of 0.1 to 250 mg/m², and very preferably at a concentration of 1 to 200 mg/m².

Deltamethrin is applied preferably (as an ingredient of the insecticidal composition of the invention, of the active ingredient-wax particles or of the spraying liquor) in an areal concentration of 0.5 mg/m² to 12 mg/m² and with particular preference from 1 mg/m² to 6.25 mg/m².

Beta-cyfluthrin is applied preferably (as an ingredient of the insecticidal composition of the invention, of the active ingredient-wax particles or of the spraying liquor) in an areal concentration of 1 mg/m² to 6.25 mg/m².

Cyfluthrin is applied preferably (as an ingredient of the insecticidal composition of the invention, of the active ingredient-wax particles or of the spraying liquor) in an areal concentration of 5 mg/m² to 12.5 mg/m².

Lambda-cyhalothrin is applied preferably (as an ingredient of the insecticidal composition of the invention, of the active ingredient-wax particles or of the spraying liquor) in an areal concentration of 1 mg/m² to 6.25 mg/m².

Bendiocarb is applied preferably (as an ingredient of the insecticidal composition of the invention, of the active ingredient-wax particles or of the spraying liquor) in an areal concentration of 50 mg/m² to 100 mg/m².

Nat pyrethrum is applied preferably (as an ingredient of the insecticidal composition of the invention, of the active ingredient-wax particles or of the spraying liquor) in an areal concentration of 10 mg/m² to 50 mg/m².

Fipronil is applied preferably (as an ingredient of the insecticidal composition of the invention, of the active ingredient-wax particles or of the spraying liquor) in an areal concentration of 1 mg/m² to 10 mg/m².

The dilution and application rate to a surface of the compositions of the invention is preferably such as to give an application of active ingredient-wax particles (based on solid material) per unit area of 0.25 mg/m² to 5000 mg/m², preferably of 0.25 mg/m² to 2500 mg/m², more preferably of 0.5 mg/m² to 1250 mg/m², and more preferably still of 5 mg/m² to 1000 mg/m².

A further subject of the invention relates to a method for freeing surfaces from pest infestation and/or for protecting surfaces from pest infestation by treatment of a surface with an insecticidal composition of the invention comprising an active ingredient-wax particle, the active ingredient in the active ingredient-wax particle comprising at least one of the following active insecticidal ingredients:

deltamethrin, and deltamethrin as an ingredient of the insecticidal composition is applied in an areal concentration of 0.5 mg/m² to 12 mg/m² to the surface, or beta-cyfluthrin, and beta-cyfluthrin as an ingredient of the insecticidal composition is applied in an areal concentration of 1 mg/m² to 6.25 mg/m² to the surface, or cyfluthrin, and cyfluthrin as an ingredient of the insecticidal composition is applied in an areal concentration of 5 mg/m² to 12.5 mg/m² to the surface, or lambda-cyhalothrin, and lambda-cyhalothrin as an ingredient of the insecticidal composition is applied in an areal concentration of 1 mg/m² bis 6.25 mg/m² to the surface, or bendiocarb, and bendiocarb as an ingredient of the insecticidal composition is applied in an areal concentration of 50 mg/m² to 100 mg/m² to the surface, or nat pyrethrum, and nat pyrethrum as an ingredient of the insecticidal composition is applied in an areal concentration of 10 mg/m² to 50 mg/m² to the surface, or fipronil, and fipronil as an ingredient of the insecticidal composition is applied in an areal concentration of 1 mg/m² to 10 mg/m² to the surface.

The compositions of the invention can be applied to any desired surface within buildings or outdoors, examples being wallpaper, concrete, cement, glazed tiles, tiles, render, stone/brickwork, timber (treated and untreated), ceramic (glazed and unglazed), straw or thatch, brick (untreated, limewashed or painted), clay minerals (e.g. terracotta), chalky, limey, gypsiferous, cement-containing and loamy surfaces, or else to plants such as lawns.

A further subject of the invention relates to surfaces treated by the method of the invention.

The examples which follow serve to illustrate the invention, and should in no way be interpreted as constituting any restriction.

EXAMPLES a) Preparation of Deltamethrin-Wax Particles 400 g of carnauba wax T4 fatty grey are melted. Then 100 g of deltamethrin are dispersed uniformly in the resultant melt, by stirring using a magnetic stirrer. The resultant liquid mixture (spraying solution) is sprayed from the reservoir by means of a pump through a two-fluid die (opening diameter 1.5/0.7 mm) into a spraying tower. The temperature of reservoir, pump and nozzle is about 90° C., while the temperature in the spraying tower is about −10 to 40° C. The particles obtained after solidification are discharged using a cyclone.

b) Preparation of a Suspension Concentrate 258 g of 1,2-propylene glycol, 516 g of Wax Emulsifier 4106 (alkoxyethoxylate mixture CAS No. [68920-66-1], Clariant International AG, Muttenz, Switzerland) MX 25% (129 g of Wax Emulsifier 4106 in demineralized water), 21.5 g of Aerosil® 200 (synthetic amorphous silica, Evonik Degussa GmbH, DE), 8.6 g of Proxel® GXL 20% (1,2-benzisothiazolin-3-one in dipropylene glycol (CAS 2634-33-5), Arch UK Biocides Ltd.), 8.6 g of citric acid (anhydrous), 4.3 g of Rhodorsil® 426 R (20-30% aqueous emulsion of polydimethyl siloxane, Bluestar Silicones, FR), 3.44 g of Preventol® D7 (liquid formulation of about 1.5% isothiazolones, Lanxess AG, DE) and 2404.56 g of demineralized water are homogenized in a vessel with stirring to give a preliminary solution. Then 215 g of deltamethrin-containing wax particles (43 g of deltamethrin in carnauba wax T 4 fatty grey) are added to this preliminary solution, with homogenization using a Silverson Homogenizer (type L4RT) at 5000 rpm, and homogenization is continued at 7700 rpm for 5 minutes more. Lastly 860 g of Kelzan® S (xanthan gum, CAS 011138-66-2, F. B. Silbermann GmbH & Co KG, DE) MX 2% (17.2 g of Kelzan® S, 0.86 g of 24-30% strength ammonia solution, 1.29 g of Proxel® GNI, 20%, 0.688 g of Preventol® D7 in demineralized water) are added with stirring using a toothed disc stirrer, and stirring is continued for 30 minutes.

c) Application of the Diluted Suspension Concentrate and Activity of this Residual Coating Against Pest Insects The suspension concentrate (10 g of deltamethrin/l) prepared in Example b) is diluted with a calculated amount of water and is applied by spraying to a timber surface in such a way that the specified amount of deltamethrin is present on said surface. For example, a 1:250 dilution of the concentrate of the invention and application of 50 ml of spraying liquor per m² gives a concentration on the surface of 2 mg of deltamethrin/m². After drying has taken place (24 hours), ants of the genus *Camponotus* spp. are exposed on the surface. After 30 minutes, they are transferred to a clean, untreated vessel. The ants are investigated at the indicated intervals of time, and the degree of destruction (mortality) is ascertained. Surprisingly, the inventive formulation gave a) a faster knockdown value and b) substantially better degrees of destruction for a low dose. The improvement in the Knockdown value and effectiveness at low concentrations is brought about by the improved bioavailability.

TABLE 1

Activity as residual coating on timber

|  | Concentration in mg deltamethrin/m² | Knockdown after 30 minutes | Knockdown after 60 minutes | Knockdown after 4 hours | Mortality after 1 day |
| --- | --- | --- | --- | --- | --- |
| Suspend ® SC (50 g deltamethrin/l, Bayer CropScience AG, DE) | 12.5 | 37 | 82 | 75 | 40 |
| Suspend ® SC | 6.25 | 45 | 97 | 85 | 70 |
| Suspend ® SC) | 4 | 22 | 85 | 67 | 25 |
| Suspend ® SC | 2 | 17 | 70 | 57 | 17 |
| Inventive SC (10 g deltamethrin/l) | 12.5 | 77 | 100 | 100 | 100 |
| Inventive SC | 6.25 | 75 | 100 | 100 | 100 |
| Inventive SC | 4 | 55 | 95 | 82 | 85 |
| Inventive SC | 2 | 27 | 82 | 85 | 55 | d) Application of the Diluted Suspension Concentrate and Activity of this Residual Coating Against Pest Insects In a further example, the suspension concentrate prepared in Example b) is diluted with water, 1:125, to give a spraying liquor in which deltamethrin is present in a concentration of 80 mg per liter of spraying liquor and the spraying liquor is subsequently applied by spraying 50 ml per m² to a concrete surface such that 4 mg/m² deltamethrin is present on this surface. After drying has taken place (24 hours), German cockroaches (*Blattella germanica*) are exposed on the surface. After 30 minutes they are transferred into a clean, untreated vessel. The cockroaches are investigated at the intervals of time indicated, and the degree of destruction is ascertained. Surprisingly, again, the inventive formulation gave a) a fastern knockdown value and b) substantially better degrees of destruction at this low dose.

Furthermore, c) a better residual effect is obtained, since after 60 weeks a 100% destruction is still achieved when the inventive invention is used. The standard formulation achieves the full destruction rate of 100% for the last time after 2 weeks.

TABLE 2

Activity as residual coating on concrete

|  |  | Age of the surface (d = days, w = weeks) | Knockdown after 1 hour | Mortality after 1 day |
| --- | --- | --- | --- | --- |
| Crackdown ® SC (10 g deltamethrin/l, Bayer CropScience AG, DE) | 4 mg/m² | 1 d | 100 | 100 |
| Crackdown ® SC | 4 mg/m² | 2 w | 30 | 100 |
| Crackdown ® SC | 4 mg/m² | 16 w | 10 | 90 |
| Crackdown ® SC | 4 mg/m² | 20 w | 0 | 80 |
| Crackdown ® SC | 4 mg/m² | 40 w | 0 | 0 |
| Crackdown ® SC | 4 mg/m² | 60 w | 0 | 0 |
| Inventive SC (10 g deltamethrin/l) | 4 mg/m² | 1 d | 100 | 100 |
| Inventive SC | 4 mg/m² | 2 w | 100 | 100 |
| Inventive SC | 4 mg/m² | 16 w | 100 | 100 |
| Inventive SC | 4 mg/m² | 20 w | 40 | 100 |
| Inventive SC | 4 mg/m² | 40 w | 60 | 100 |
| Inventive SC | 4 mg/m² | 60 w | 10 | 100 | e) Use of Other Active Ingredients

Example e) illustrates that other active ingredients as well can be used successfully in the context of this invention (as a diluted suspension concentration, i.e. as a spraying liquor of the invention). In addition to deltamethrin, both bendiocarb and beta-cyfluthrin and cyfluthrin can be encapsulated. Table 3a shows knockdown after 1 h and degree of destruction after 24 h (in each case in %) on *Blattella germanica* after 30-minute exposure on various surfaces which were treated with the indicated active ingredients at the indicated standard concentration. Table 3b shows Knockdown after 1 h and degree of destruction after 24 h (indicated in % every time) on *Blattella germanica* 30 minutes after treating surfaces with the indicated active insecticidal ingredients at a reduced concentration of active ingredient.

TABLE 3a

Activity of different insecticides at the standard concentration

| | Bendiocarb 100 mg/m² | | | Deltamethrin 12.5 mg/m² | | | Beta-cyfluthrin 12.5 mg/m² | | | cyfluthrin 25 mg/m² | | |
|---|---|---|---|---|---|---|---|---|---|---|---|---|
| | Timber | Cement | Tile | Timber | Cement | Tile | Timber | Cement | Tile | Timber | Cement | Tile |
| Knockdown after 1 h | 60 | 100 | 100 | 100 | 100 | 100 | 100 | 100 | 100 | 100 | 100 | 100 |
| Mortality after 24 h | 100 | 100 | 100 | 100 | 100 | 100 | 100 | 100 | 100 | 100 | 100 | 100 |

TABLE 3b

Activity of different insecticides at reduced concentration

| | Bendiocarb 50 mg/m² | | | Deltamethrin 4 mg/m² | | | Beta-Cyfluthrin 4 mg/m² | | | cyfluthrin 8 mg/m² | | |
|---|---|---|---|---|---|---|---|---|---|---|---|---|
| | Timber | Cement | Tile | Timber | Cement | Tile | Timber | Cement | Tile | Timber | Cement | Tile |
| Knockdown after 1 h | 50 | 90 | 100 | 100 | 100 | 100 | 100 | 100 | 100 | 100 | 100 | 100 |
| Mortality after 24 h | 100 | 100 | 100 | 100 | 100 | 100 | 100 | 100 | 100 | 100 | 100 | 100 | f) Suitability for a Wide Variety of Pest Insects

Example f) illustrates that other pest insects as well can be successfully controlled in the context of this invention. Table 4 shows the degree of destruction after 24 hours, after just 5-minute exposure on a timber surface which was treated with the indicated formulations at the indicated concentration.

TABLE 4

Activity against different pest insects

| | Conc. in mg DLT/m² | Camponotus spp | Solenopsis xyloni | Blattella germanica | Tribolium confusum | Musca domestica |
|---|---|---|---|---|---|---|
| Suspend ® SC (50 g deltamethrin/l, Bayer CropScience AG, DE) | 12.5 | 40 | 18 | 100 | 52 | 100 |
| Suspend ® SC | 6.25 | 70 | 15 | 100 | 70 | 100 |
| Suspend ® SC | 4 | 25 | 18 | 100 | 96 | 100 |
| Suspend ® SC | 2 | 18 | 28 | 100 | 4 | 100 |
| Inventive SC (10 g deltamethrin/l) | 12.5 | 100 | 100 | 100 | 70 | 100 |
| Inventive SC | 6.25 | 100 | 98 | 100 | 56 | 100 |
| Inventive SC | 4 | 85 | 90 | 100 | 81 | 100 |
| Inventive SC | 2 | 55 | 88 | 100 | 33 | 100 |

All documents cited herein (e.g., patents, published applications, non-patent literature, etc.) are hereby incorporated by reference in their entireties.

The invention claimed is:

1. A suspension concentrate comprising:
(a) at least one active insecticidal ingredient;
(b) a wax: (i) having a melting point of 50 to 160° C., (ii) containing said active insecticidal ingredient and (iii) in the form of particles having a particle size of 5 to 40 μm; and
(c) water;
wherein the ratio, in percent by weight of the suspension concentrate, is about 0.5% to 5% by weight of the active insecticidal ingredient to 2% to 13% by weight of the wax, to 65% to 90% by weight of water;
wherein the suspension concentrate is made by a process comprising: (i) melting the wax; (ii) incorporating the active insecticidal ingredient uniformly into the melted wax to form a mixture as spraying solution; (iii) the spraying solution is atomized from a heated reservoir, which has been heated to at least 90° C., into a cold environment in a spraying tower, whereby the sprayed droplets of the spraying solution are solidified and solid active insecticide-containing wax particles are obtained; and (iv) dispersing the solid active insecticide-containing wax particles in water to form the suspension concentrate; and
wherein the active insecticidal ingredient is in the form of crystals present at the surface of said wax particles.

2. The suspension concentrate according to claim 1, wherein the active insecticidal ingredient is deltamethrin, cyfluthrin, cypermethrin, bendiocarb, bifenthrin, permethrin, lambda cyhalothrin, gamma-cyhalothrin, etofenprox, pyrethrum, indoxacarb, carbaryl, fipronil, metaflumizone, azadirachtin, flubendiamide, chloranthraniliprole, boric acid, borax, imidacloprid, clothianidin, dinotefuran, acetamiprid, fenpyroximate, tolfenpyrad, spinosad, or combinations thereof.

3. The suspension concentrate according to claim 1, wherein the wax is carnauba wax, montan wax, or combinations thereof.

4. The suspension concentrate, according to claim 1, further comprises nonionic surfactants selected from the group consisting of polyethylene glycol ethers of linear alcohols, reaction products of fatty acids with ethylene oxide, propylene oxide, and combinations thereof.

5. The suspension concentrate, according to claim 1, further comprises an additive, wherein said additive is a dispersing assistant, release agent, frost preventive, foam inhibitor, preservative, antioxidant, spreader, colorant, thickener, acid or base pH adjustor, or combinations thereof.

6. The suspension concentrate, according to claim 1, does not comprise pheromones, carbohydrate polymers, oil-absorbing substances, inorganic carriers, evaporation inhibitors, fertilizers, liquid mineral oils, or combinations thereof.

7. A porous surface comprising the suspension concentrate of claim 1.

8. An alkaline porous surface comprising the suspension concentrate of claim 1.

* * * * *